(12) United States Patent
Harada

(10) Patent No.: US 8,232,536 B2
(45) Date of Patent: Jul. 31, 2012

(54) PARTICLE BEAM IRRADIATION SYSTEM AND METHOD FOR CONTROLLING THE PARTICLE BEAM IRRADIATION SYSTEM

(75) Inventor: Hisashi Harada, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 31 days.

(21) Appl. No.: 13/058,963

(22) PCT Filed: May 27, 2010

(86) PCT No.: PCT/JP2010/058979
§ 371 (c)(1),
(2), (4) Date: Feb. 14, 2011

(87) PCT Pub. No.: WO2011/148486
PCT Pub. Date: Dec. 1, 2011

(65) Prior Publication Data
US 2012/0056098 A1    Mar. 8, 2012

(51) Int. Cl.
*H01J 37/09* (2006.01)
*G21K 5/04* (2006.01)

(52) U.S. Cl. ............. 250/493.1; 250/396 R; 250/491.1; 250/492.1; 250/492.2; 250/492.22; 378/65; 378/137; 378/156; 600/1; 600/2

(58) Field of Classification Search ............. 250/396 R, 250/396 ML, 491.1, 492.1, 492.2, 492.22, 250/492.3, 493.1; 378/65, 137, 156; 600/1, 600/2

See application file for complete search history.

(56) References Cited

U.S. PATENT DOCUMENTS 4,537,507 A * 8/1985 Hess .............................. 356/336
(Continued)

FOREIGN PATENT DOCUMENTS

JP    2001-212253 A    8/2001
(Continued)

OTHER PUBLICATIONS

International Search Report (PCT/ISA/210) for PCT/JP2010/058979 dated Jun. 29, 2010.

*Primary Examiner* — David A Vanore
(74) *Attorney, Agent, or Firm* — Buchanan Ingersoll & Rooney PC

(57) ABSTRACT

There is provided a particle beam irradiation system so as to provide the dose distribution having more accuracy. An irradiation control part comprises an energy setting controller that sets the energy of a charged particle beam, a beam scanning controller that controls a beam scanner, and a beam diameter changer to control a beam diameter changer, wherein the irradiation control part sets a beam diameter of the charged particle beam to be a first beam diameter by the beam diameter changer, the charged particle beam is scanned step-wise by the beam scanning controller so as to irradiate the charged particle beam on a predetermined region of the irradiation target, after that, the beam diameter of the charged particle beam is set by the beam diameter controller to be a second beam diameter that is different from the first beam diameter, and the charged particle beam is scanned step-wise by the beam scan controller so as to control the charged particle beam to irradiate on a region that is overlapped with at least a part of the predetermined part of the irradiation target.

9 Claims, 16 Drawing Sheets

U.S. PATENT DOCUMENTS

| | | | | |
|---|---|---|---|---|
| 4,754,147 A | * | 6/1988 | Maughan et al. | 250/505.1 |
| 4,868,843 A | * | 9/1989 | Nunan | 378/152 |
| 6,218,675 B1 | * | 4/2001 | Akiyama et al. | 250/492.3 |
| 6,433,336 B1 | * | 8/2002 | Jongen et al. | 250/305 |
| 6,472,834 B2 | * | 10/2002 | Hiramoto et al. | 315/501 |
| 6,641,705 B2 | * | 11/2003 | Phaneuf et al. | 204/192.34 |
| 6,825,476 B2 | * | 11/2004 | Adamec | 250/398 |
| 7,102,144 B2 | | 9/2006 | Matsuda et al. | |
| 7,122,978 B2 | * | 10/2006 | Nakanishi et al. | 315/500 |
| 7,157,703 B2 | * | 1/2007 | Nakasuji et al. | 250/311 |
| 7,525,104 B2 | * | 4/2009 | Harada | 250/396 R |
| 7,792,249 B2 | * | 9/2010 | Gertner et al. | 378/65 |
| 8,129,699 B2 | * | 3/2012 | Balakin | 250/492.3 |
| 2001/0053605 A1 | * | 12/2001 | Phaneuf et al. | 438/689 |
| 2003/0011760 A1 | * | 1/2003 | Vaez-Iravani et al. | 356/237.2 |
| 2003/0075686 A1 | * | 4/2003 | Adamec | 250/398 |
| 2003/0213922 A1 | * | 11/2003 | Gordon et al. | 250/492.1 |
| 2004/0159787 A1 | * | 8/2004 | Nakasuji et al. | 250/311 |
| 2008/0067401 A1 | | 3/2008 | Harada | |
| 2009/0161826 A1 | * | 6/2009 | Gertner et al. | 378/65 |
| 2010/0091948 A1 | * | 4/2010 | Balakin | 378/65 |
| 2010/0127184 A1 | * | 5/2010 | Balakin | 250/396 R |
| 2010/0181479 A1 | * | 7/2010 | Knippelmeyer et al. | 250/310 |
| 2010/0213384 A1 | * | 8/2010 | Furukawa et al. | 250/396 ML |
| 2010/0266100 A1 | * | 10/2010 | Balakin | 378/65 |
| 2011/0118529 A1 | * | 5/2011 | Balakin | 600/1 |
| 2011/0118531 A1 | * | 5/2011 | Balakin | 600/1 |
| 2011/0147608 A1 | * | 6/2011 | Balakin | 250/396 R |
| 2011/0150180 A1 | * | 6/2011 | Balakin | 378/65 |
| 2011/0182410 A1 | * | 7/2011 | Balakin | 378/65 |
| 2011/0196223 A1 | * | 8/2011 | Balakin | 600/407 |
| 2011/0233423 A1 | * | 9/2011 | Balakin | 250/454.11 |
| 2011/0313232 A1 | * | 12/2011 | Balakin | 600/1 |
| 2012/0056098 A1 | * | 3/2012 | Harada | 250/396 R |

FOREIGN PATENT DOCUMENTS

| | | |
|---|---|---|
| JP | 2006-346120 A | 12/2006 |
| WO | WO 2006/082651 A1 | 8/2006 |

* cited by examiner

PARTICLE BEAM IRRADIATION SYSTEM AND METHOD FOR CONTROLLING THE PARTICLE BEAM IRRADIATION SYSTEM

TECHNICAL FIELD

The present invention relates to a particle beam irradiation system applied to a treatment of a cancer or the like.

BACKGROUND ART

The treatment of a cancer is one of applications of radiation beam. Recently, particle beam therapy in which a heavy particle beam such as a proton beam or a carbon beam is irradiated on the cancer cell has been attracted attention. Referring to FIGS. 14 to 16, the characteristic of a particle beam irradiation in which the particle beam is irradiated to kill a cancer cell will be described. In a case where thin diameter pencil beams of various kinds of radiation beams are irradiated on a human body, the dose distribution of the radiation beam in the human body changes as shown in FIG. 14. As shown in FIG. 14, among various kinds of radiations, a radiation beam with a small mass, such as an X-ray or a gamma ray, has a relative dose which becomes maximum in a portion close to the surface of the body, and is decreased as the depth from the surface of the body is increased. On the other hand, a particle beam with a large mass, such as a proton beam or a carbon beam, has a relative dose which has a peak value at a position where the beam stops at a deep portion from the surface of the body, that is, immediately before the range of the particle beam. This peak value is called the Bragg Peak (BP).

Particle beam cancer treatment is such that this Bragg peak BP is irradiated to a tumor formed in a human organ and the treatment of the cancer is performed. In addition to the cancer, it can also be used for a case where a deep portion of a body is treated. A region to be treated, including a tumor, is generally called an irradiation target (TV). The position of the Bragg peak BP is determined by the energy of an irradiated particle beam, and as the energy of the particle beam becomes high, the Bragg peak BP is formed at a deep position. In the particle beam treatment, it is necessary that the particle beam is made to have a uniform dose distribution over the whole of the irradiation target to be irradiated. In order to give the Bragg peak BP to the whole region of the irradiation target, "spread of irradiation field" of the particle beam is performed.

This "spread of irradiation field" is performed in three directions of an X-axis, a Y-axis and a Z axis perpendicular to each other. When the irradiation direction of the radiation beam is made the direction of the Z-axis, the "spread of irradiation field" is first performed in the Z-axis direction. The "spread of irradiation field" in the irradiation direction of the radiation beam is generally called depth direction irradiation field spread. The second "spread of irradiation field" is such that the irradiation field spread is performed in the X-axis and Y-axis directions, and since the irradiation field spread is performed in the lateral direction perpendicular to the depth direction, it is generally called lateral direction irradiation field spread.

The depth direction irradiation field spread is performed to spread the Bragg peak BP, which is in the irradiation direction of the particle beam, in the depth direction since the width of the Bragg peak BP in the irradiation direction of the particle beam is narrow as compared with the extent of the irradiation target in the depth direction. On the other hand, the lateral direction irradiation field spread is performed to spread the Bragg peak BP in the direction perpendicular to the irradiation direction since the diameter of the particle beam is smaller than the size of the irradiation target in the direction perpendicular to the irradiation direction. With respect to the depth direction irradiation field spread and the lateral direction irradiation field spread, various kinds of methods have been proposed so far. Recently, a spot scanning technique has attracted attention.

In spot scanning technique, as a lateral direction irradiation field spread method, there is a method in which a deflection electromagnet provided at the upstream portion of a particle beam irradiation part of a particle beam irradiation apparatus is used to scan the particle beam in the XY plane, and the irradiation position of the particle beam is moved with the lapse of time to obtain a wide irradiation field. In this method, a uniform dose distribution can be obtained by suitably overlapping adjacent irradiation spots of small diameter pencil beams. Scanning methods of a pencil beam include a raster method of performing scanning continuously with respect to time, and a spot method of performing a step-like scanning with respect to time.

As the depth irradiation field spread method, there is a method in which the energy of the particle beam itself irradiated from a particle beam irradiation apparatus is controlled. In this method, the energy of the particle beam is controlled by changing the acceleration energy of an accelerator to accelerate the particle beam, or the energy of the particle beam is changed by inserting a tool called a range shifter so as to cross the particle beam. There is also a method in which both the control by the accelerator and the range filter are used.

In the depth direction irradiation field spread method, the particle beam is made the beam having the energy of specified intensity, and after the Bragg peak BP with a uniform dose is irradiated to one irradiation layer of the irradiation target, the energy of the particle beam is changed, and the Bragg peak BP is irradiated to next irradiation layer in the irradiation target TV. Such operation is repeated plural times, and the Bragg peak BP of the particle beam is irradiated to the plural irradiation layers, so that the spread-out Bragg peak SOBP having a desired width in the beam irradiation direction can be obtained. The depth direction active irradiation field spread method is a method in which the energy of the particle beam is changed in the state where the particle beam is not moved in the X and Y-axis directions and is fixed to a definite irradiation position.

In order to obtain the spread-out Bragg peak SOBP having the desired width, it is necessary to suitably adjust the dose of each irradiation layer of the irradiation target TV. FIG. 15 shows an example of dose distribution of each irradiation layer. In FIG. 15, the vertical axis indicates the relative dose, and the horizontal axis indicates the depth in the body. Each of plural curve lines indicated by broken line indicates the depth direction dose distribution of each beam having different energy, that is, the dose distribution of each irradiation layer, in a case where beams having different energy are irradiated. The dose that is obtained by integrating the dose of each irradiation layer is the dose which is applied to the depth direction, and is shown by a solid curve line in FIG. 15. The solid curve line is the spread-out Bragg peak obtained by the above-mentioned irradiation field spread method. A particle beam irradiation method in which the lateral direction irradiation field spread method and the depth direction irradiation field spread method are combined is known as the spot scanning technique.

On the other hand, in a treatment of cancer, it is necessary to kill a cancer cell without affecting normal cells. The details will be described referring to FIG. 16. In FIG. 16, the horizontal axis indicates the dose of particle beam, a dotted line indicates the death ratio of tumor cell to the dose and an alternate long and short dash line indicates the ratio of adverse effect of normal cell to the dose. In a treatment of cancer, it is necessary to increase the death ratio of tumor cell and to decrease the ratio of adverse effect to normal cell. The cure ratio is maximum at the dose where the difference between the death ratio of tumor cell and the ratio of adverse effect to normal cell is large (the dose that is shown as an optimal dose in FIG. 16). Further, since normal cells exist outside of therapeutic area, it is necessary to decrease the dose to be irradiated outside of therapeutic area as much as possible. That is, it is necessary to make the dose distribution in a boundary region to be steep. In a spot scanning technique, in order to make the dose distribution in a boundary region steep, the technology to make the spot size (beam diameter) of a particle beam to be irradiated on a boundary region small was proposed (for example Patent Document 1).

In order to compensate the deviation of irradiation caused by moving the position of diseased site due to the respiration of the patient, a method in which irradiation is performed plural times at the same spot in each irradiation layer for time-dividing was proposed (for example, Patent Document 2, FIG. 11). Further, in Patent Document 2, a technique for controlling the irradiation dose synchronized with the respiration phase, in view of the moving of the position of diseased site due to the respiration of the patient, was proposed.

PRIOR ART REFERENCES

PATENT DOCUMENT

Patent Document 1: Patent Application Laid-Open No. 2001-212253 (FIG. 5, FIG. 6)
Patent Document 2: National Publication of International Patent Application No. 2006-082651 (FIG. 11)

DISCLOSURE OF THE INVENTION

Problems to be Solved by the Invention

According to the irradiation method disclosed by the Patent Document 1, regions where beams having different diameters are irradiated are divided into a group, and a border of regions where beams having different diameters are irradiated is generated. Therefore, in the border, it is difficult to dispose spots having different beam diameters.

In order to solve the above-mentioned problems, an objective of the present invention is to provide a particle beam irradiation system by spot scanning irradiation method in which increase of irradiation time is suppressed, positioning of beams is simple and the dose having high accuracy can be obtained.

Means for Solving the Problems

The particle beam irradiation system according to the present invention comprises a particle beam generation part; a particle beam irradiation part where a charged particle beam that is generated in the particle beam generation part is irradiated on the irradiation target and; an irradiation control part that controls the charged particle beam to be irradiated, wherein the particle beam irradiation part comprises a beam scanner that scans the charged particle beam laterally in two dimension that is perpendicular to the irradiation direction of the charged particle beam, and a beam diameter changer that changes the beam diameter of the charged particle beam; the irradiation control part comprises an energy setting controller that sets the energy of the charged particle beam: a beam scanning controller that controls the beam scanner; and the beam diameter controller that controls the beam diameter changer, wherein the irradiation control part sets the beam diameter of the charged particle beam by the beam diameter controller to be a first beam diameter, the charged particle beam is scanned step-wise by the beam scanning controller so as to irradiate the charged particle beam on a predetermined region of the irradiation target, after that, the beam diameter of the charged particle beam is set by the beam diameter controller to be a second diameter that is different from the first beam diameter, and the charged particle beam is scanned step-wise by the beam scan controller so as to control the charged particle beam to irradiate on a region that is overlapped with at least a part of the predetermined part of the irradiation target.

Advantage of the Invention

In the present invention, since a part of region of the irradiation target is irradiated with beams having different beam diameters plural times, a border of regions where beams having different beam diameters are irradiated is not generated. Consequently, it is simple to dispose beams, and in the region where irradiation is performed plural times, the dose distribution having more accuracy can be obtained. Further, irradiation is performed plural times only in a region where a great dose of irradiation is applied, therefore, irradiation time will not be increased.

EMBODIMENTS FOR CARRYING OUT THE INVENTION

Embodiment 1

Figure 1:
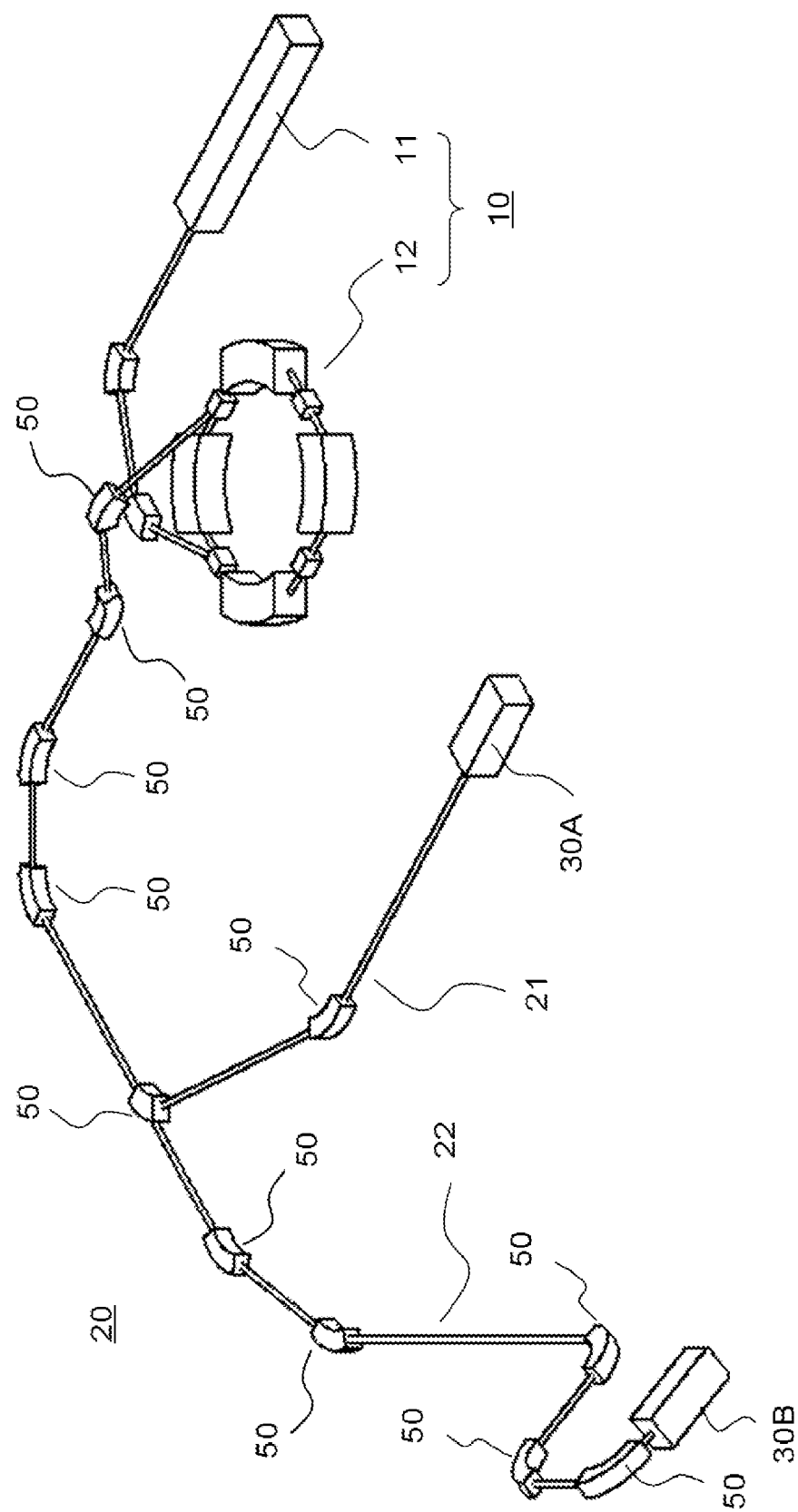
FIG. 1 is a bird's-eye view schematically illustrating an example of whole configuration of the particle beam irradiation system to which the present invention is applied.
Figure 2:
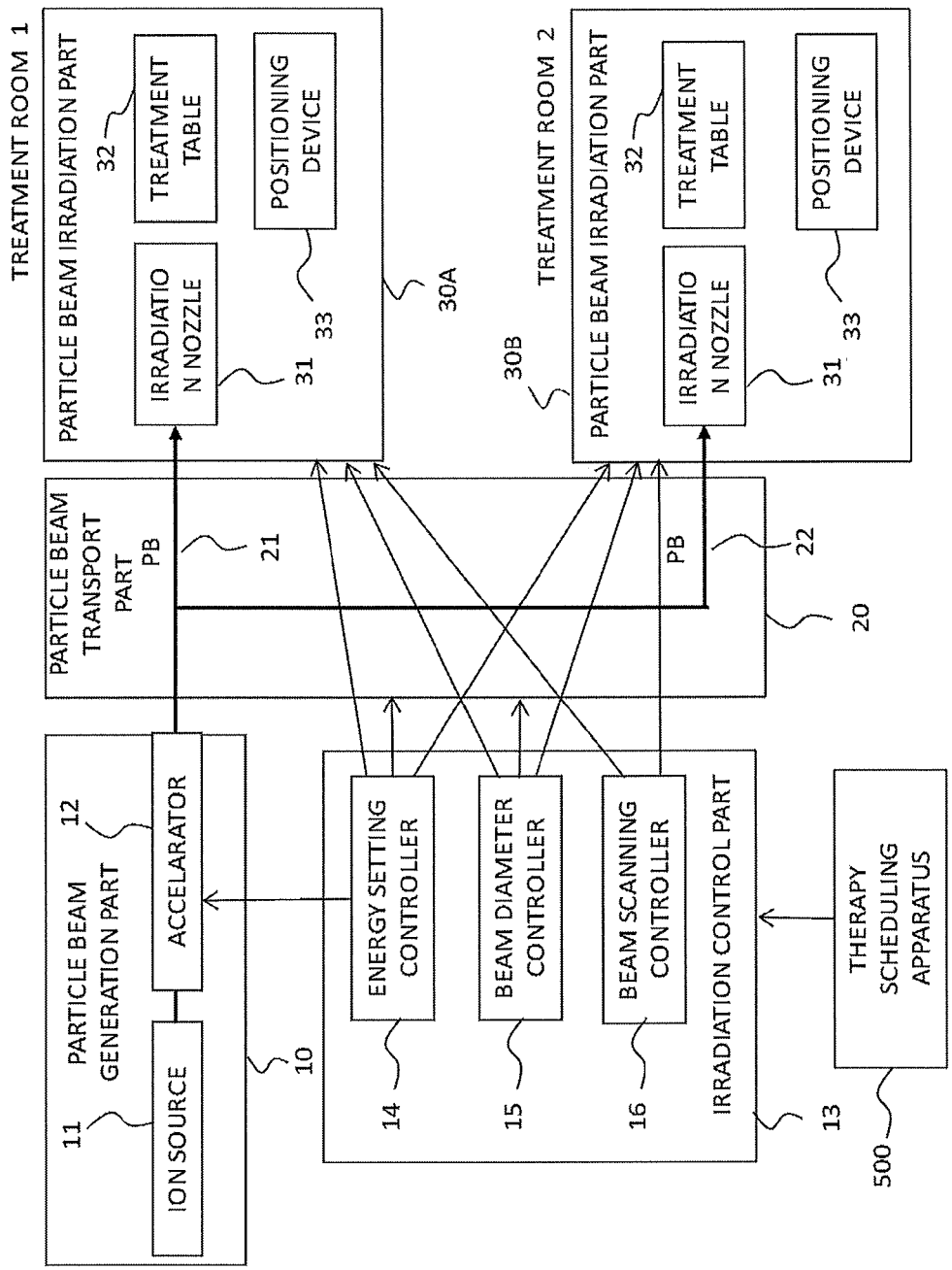
FIG. 2 is a block diagram schematically illustrating the configuration of the particle beam irradiation system according to Embodiment 1 of the present invention.

FIG. 1 is a bird's-eye view schematically illustrating the whole configuration of the particle beam irradiation system according to Embodiment 1 of the present invention, and FIG. 2 is a block diagram schematically illustrating the configuration of the particle beam irradiation system according to Embodiment 1 of the present invention which includes a controlling device in addition to the whole configuration shown in a bird's-eye view of FIG. 1. As shown in FIGS. 1 and 2, Embodiment 1 of the particle beam irradiation system includes a particle beam generation part 10, a particle beam transport part 20, and two particle beam irradiation parts 30A and 30B. For reasons of application of radiation safety management and the like, the particle beam generation part 10 and the particle beam irradiation parts 30A and 30B are installed in individual shielded rooms. The particle beam transport part 20 connects the particle beam generation part 10 to the respective particle beam irradiation parts 30A and 30B. The particle beam transport part 20 includes particle beam transport passages 21 and 22 to transport the particle beam generated in the particle beam generation part 10 to the respective particle beam irradiation parts 30A and 30B. The particle beam transport part 20 has a deflection electromagnet 50 for changing the direction of a particle beam and is constructed so as for a particle beam to pass through vacuum ducts. The particle beam irradiation parts 30A and 30B irradiate the particle beam PB to target regions TV of patients.

The particle beam generation part 10 includes an ion source 11 and an accelerator 12. The ion source 11 generates the particle beam with mass, such as a proton beam or a carbon beam. The accelerator 12 accelerates the particle beam generated in the ion source 11, and forms the particle beam PB. The accelerator 12 electrically connects to an energy setting controller 14 provided in an irradiation control part 13. The energy setting controller 14 supplies an energy setting signal to the accelerator 12 and sets the accelerating energy so as to set and control the energy of particle beam PB emitted from the accelerator 12. Consequently, the energy setting controller 14 controls the depth direction irradiation field spread, that is, the depth direction irradiation position of a particle beam. The energy setting controller 14 generally sets the energy of particle beam based on the data received by a therapy scheduling apparatus 500 so as to control to overlap plural irradiation layers having different ranges in the depth direction. The energy of particle beam is changed for each irradiation layer and a spread-out Bragg peak SOBP is formed in the irradiation direction of a particle beam PB, that is, in the Z-axis direction. An irradiation control part 13 has a beam diameter controller 15 to transmit the signal for controlling a beam diameter to an irradiation nozzle 31. Further, the irradiation control part 13 has a beam scanning controller 16 to transmit the signal for scanning a beam to the irradiation nozzle 31.

The particle beam irradiation parts 30A and 30B constitute a treatment room 1 and a treatment room 2, respectively. The two particle beam irradiation parts 30A and 30B include the irradiation nozzle 31, a treatment table 32 and a positioning device 33, respectively. The treatment table 32 is used for keeping a patient in the state of a dorsal position or a sitting position, and the positioning device 33 is used for confirming the position of an affected organ by an X-ray apparatus or the like. The irradiation nozzle 31 irradiates the particle beam PB transported to the particle beam irradiation parts 30A and 30B to the irradiation target TV of the patient on the treatment table 32.

Figure 3:
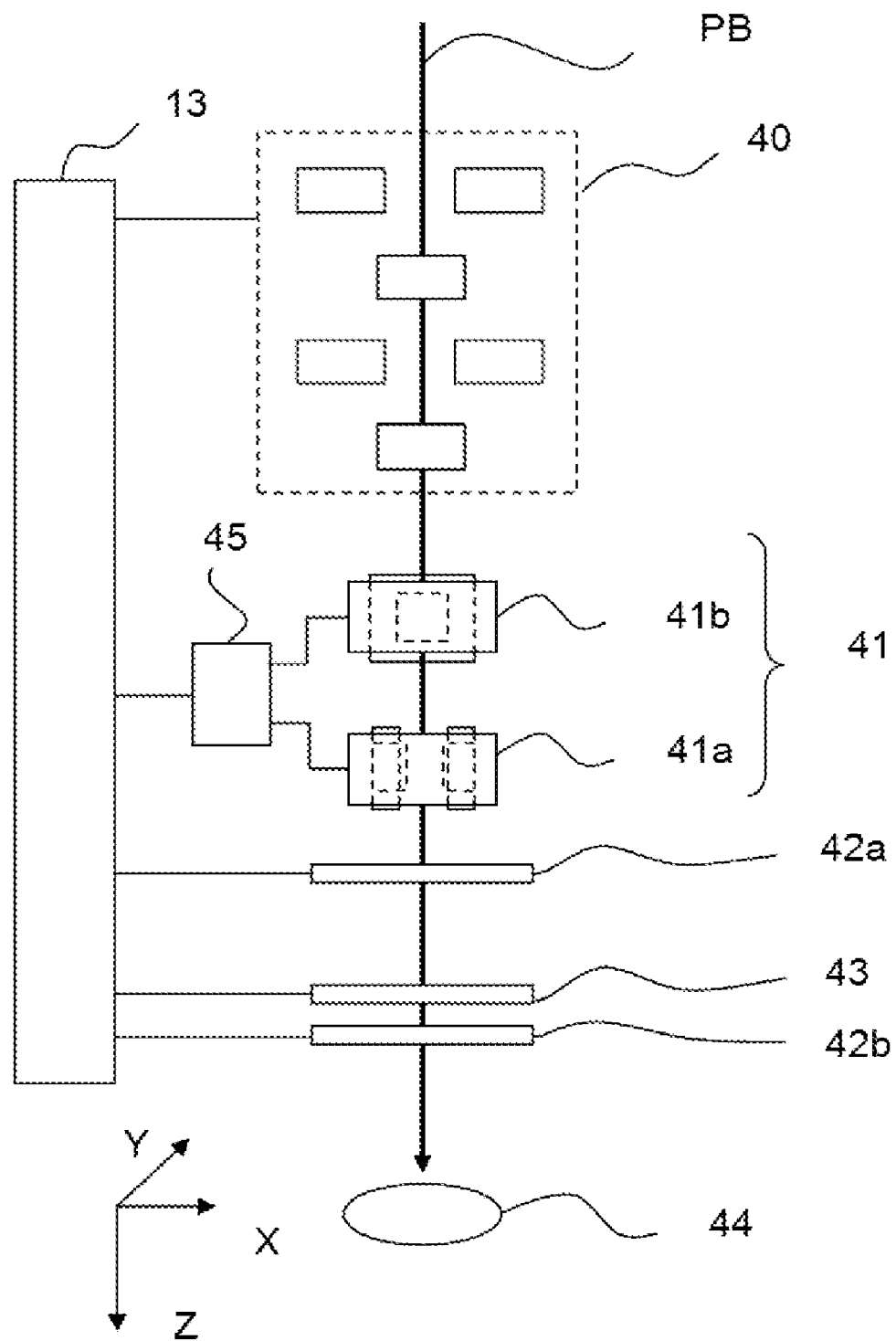
FIG. 3 is a block diagram illustrating the specific configuration of an irradiation nozzle of particle beam irradiation system according to Embodiment 1 of the present invention.

FIG. 3 shows the specific structure of the irradiation nozzle 31 of each of the particle beam irradiation parts 30A and 30B. The irradiation nozzle in FIG. 3 is indicated by symbol 31. The irradiation nozzle shown in FIG. 3 has a beam diameter changer 40 for changing a beam diameter of the particle beam PB. Here, as a beam diameter changer, a quadruple magnet that is generally used for changing a beam diameter of the particle beam is used. The beam diameter changer 40 changes a beam diameter of the particle beam PB that is controlled by the signal transmitted from a beam diameter controlling part of the irradiation control part 13. Further, the irradiation nozzle 31 has deflection electromagnets for scanning 41a and 41b to scan the particle beam PB whose diameter was changed by the beam diameter changer, in the lateral direction perpendicular to the irradiation direction of the particle beam BP, that is, the X-axis and Y-axis directions, beam position monitors 42a and 42b to monitor the irradiation position of the particle beam PB and a dose monitor 43 to monitor the irradiation doze of the particle beam PB.

An arrow PB of FIG. 3 indicates the irradiation direction of the particle beam PB. The deflection electromagnets for scanning 41a and 41b are disposed to be adjacent to each other in the irradiation direction. The beam position monitors 42a and 42b are disposed to be spaced from each other in the irradiation direction, and the dose monitor 43 is placed between the beam position monitors 42a and 42b and near the beam position monitor 42b.

The deflection electromagnets for scanning 41a and 41b shown in FIG. 3 constitute a lateral direction active irradiation field spread means 41 (also called as a beam scanner) for spreading the Bragg peak BP of the particle beam PB in the lateral direction perpendicular to the irradiation direction. The beam scanner 41 forms the spread-out SOBP in the lateral direction perpendicular to the irradiation direction of the particle beam BP, that is, the X-axis and Y-axis directions. Specifically, the particle beam PB is scanned in the lateral direction, that is, on the XY plane, the irradiation spots are superimposed in the lateral direction, and the spread-out SOBP is formed on the XY plane. The beam scanner 41 is controlled by a beam scanning controller 16 provided in the irradiation control part 13 shown in FIG. 2.

Figure 4A:
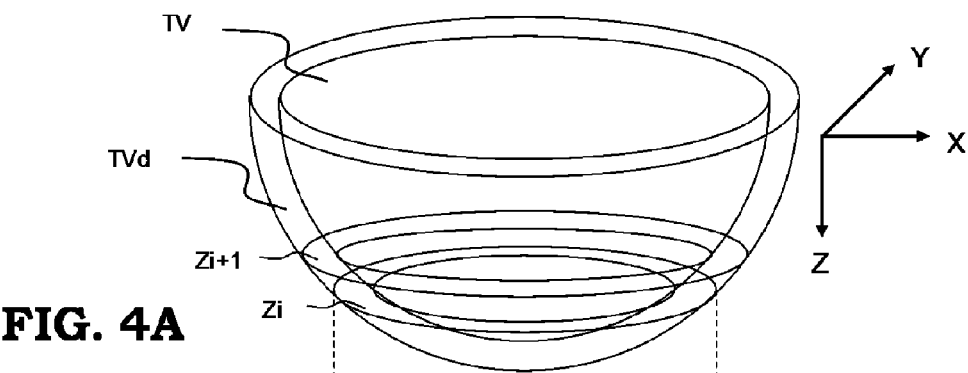
FIG. 4 is a schematic diagram for explaining the control method of particle beam irradiation system according to Embodiment 1 of the present invention.
Figure 4B:
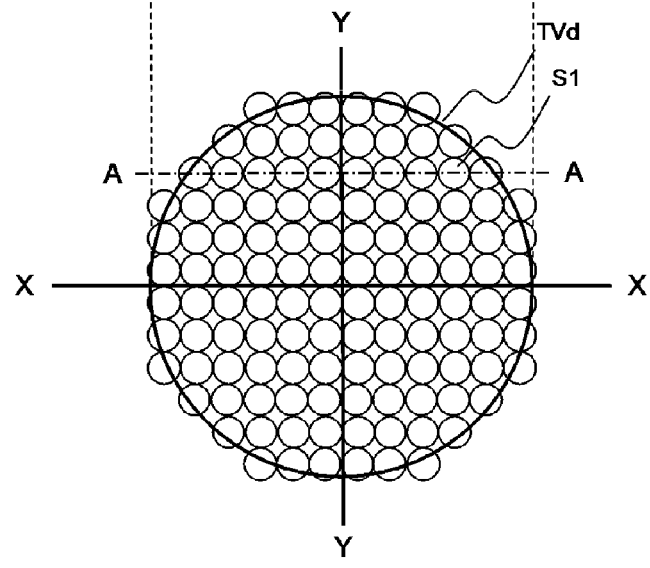
Figure 4C:
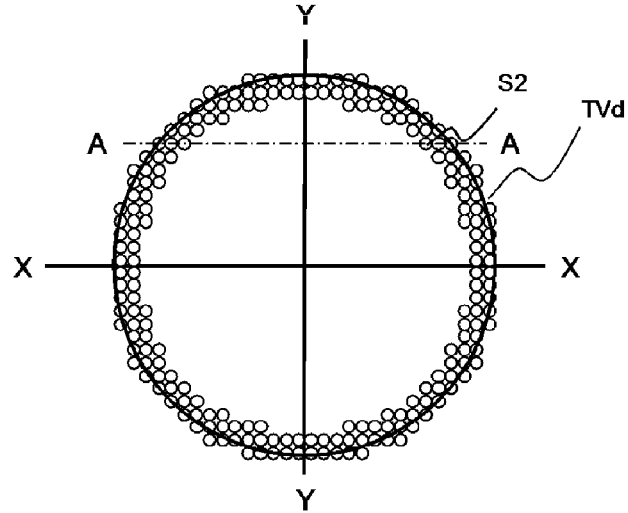

In the present invention, irradiation of a certain particle beam energy, that is, irradiation in one irradiation layer is performed by plural beams having different beam diameters. Referring FIGS. 4 and 5, the details will be described. FIG. 4A is a schematic diagram of irradiation target TV, here, a semicircular irradiation target TV is supposed. The deepest layer TVd is a surface part (boundary part) of this semicircular irradiation target TV. The dose of the particle beam is given to the whole region of this semicircular irradiation target, that is, in the depth direction (the z-axis direction), the irradiation field is spread by changing the particle beam energy, and in the lateral direction (X, Y-axis direction), the irradiation field is spread by scanning the particle beam with the beam scanner 41. In FIG. 4A, an irradiation layer indicated by Zi is an irradiation layer which is irradiated with a certain particle beam energy Ei, and an irradiation layer indicated by Z i+1 is an irradiation layer which is irradiated with a particle beam energy that is changed from Ei to E i+1, wherein E i+1 is smaller than Ei. Hereinafter, a case in which a layer Zi shown in FIG. 4 A is irradiated with certain particle beam energy Ei will be described. FIGS. 4B and 4C are diagrams showing the irradiation method of particle beam PB of spot scanning technique according to the present invention in which the Zi layer irradiated with the particle beam energy Ei. In FIGS. 4B and 4C, plural small circles S1 and S2 indicate irradiation spots corresponding to the diameter of the particle beams PB. Although these irradiation spots are actually scanned in a way such that the irradiation spots adjacent to each other partially overlap with each other, for simplification of the drawings, they are shown in a state where there is no overlap.

Further, in FIGS. 4B and 4C, the X-axis in the lateral direction relative to the particle beam PB is indicated by a line X-X, and the Y-axis is indicated by a line Y-Y. The deepest layer TVd of irradiation target region TV shown in FIG. 4A is indicated in FIGS. 4B and 4C by a large circle TVd. Plural irradiation spots which are disposed in the circle TVd and which partially overlap the circle TVd are indicated by a small circle S1 and S2 indicated by a solid line.

The beam diameter of a particle beam which irradiates on the irradiation spot S1 shown in FIG. 4B is different from the beam diameter of a particle beam which irradiates on the irradiation spot S2 shown in FIG. 4C. The diameter of the irradiation spot S2 shown in FIG. 4C is smaller than that of the irradiation spot S1. First, the beam diameter is set to be the diameter of the irradiation spot S1 shown in FIG. 4B by the beam diameter changer 40. Irradiation with the particle beam having the diameter of the irradiation spot S1 is performed at each spot position until the irradiation dose reaches the target irradiation dose by measuring the irradiation dose with the dose monitor 43. Spot positions are moved by scanning the particle beam PB with the beam scanner 41. That is, the particle beam is irradiated at a spot position until the irradiation dose reaches the target irradiation dose. After the target irradiation dose is reached, by changing an exciting current of the deflection electromagnets for scanning 41a and 41b, the irradiation spot S1 is moved to the adjacent spot position and the particle beam is irradiated until the target irradiation dose at the spot position is reached. This operation is repeated, and the particle beam having a diameter of the irradiation spot S1 is irradiated at the whole region of Zi layer shown in FIG. 4A, that is, at all spot positions indicated by a small circle shown in FIG. 4B.

After the irradiation in the Zi layer with the irradiation spot S1 is completed, the beam diameter is changed by the beam diameter changer 40 to be the diameter of the irradiation spot S2 shown in FIG. 4C. The diameter of the irradiation spot S2 is set to be smaller than that of the irradiation spot S1. The irradiation with this irradiation spot S2 is performed only in the peripheral part of the Zi layer in which the Zi layer is the deepest layer, as shown by a small circle in FIG. 4C.

Figure 5:
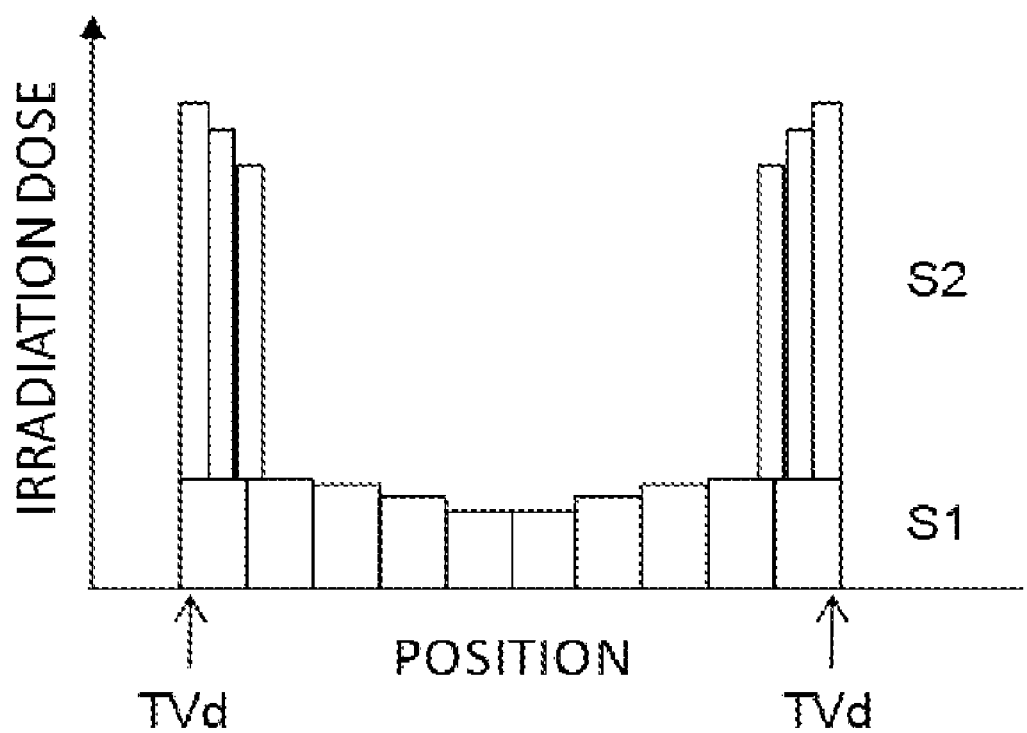
FIG. 5 is a diagram for explaining the irradiation dose irradiated by the control method of particle beam irradiation system according to Embodiment 1 of the present invention.

The distribution of total of dose irradiated with the irradiation spot S1 and the irradiation spot S2 is shown in FIG. 5. FIG. 5 shows the distribution of dose performed in the line A-A in the Zi layer shown in FIG. 4B and FIG. 4C. In FIG. 5, the horizontal axis indicates a position on the line A-A, and the vertical axis indicates the irradiation dose at the position. As shown in FIG. 5, a degree of a required amount of dose for a part of the Zi layer other than the deepest layer is irradiated including the peripheral part of the deepest layer without significantly changing the irradiation dose (per unit area) irradiated with the irradiation spot S1. The irradiation with the irradiation spot S2 is only performed in the deepest layer part of the Zi layer, and the total dose, that is, the dose performed with the irradiation spot S2 and that performed with the irradiation spot S1 are combined, is made to be the required amount of dose to be given to the part. As a result, as shown in FIG. 5, a great dose of irradiation is performed to a peripheral part which is the deepest layer. Further, in this peripheral part, there are many spots irradiated with the irradiation spots S2 having a small diameter, therefore, a detailed distribution of dose can be formed.

Figure 15:
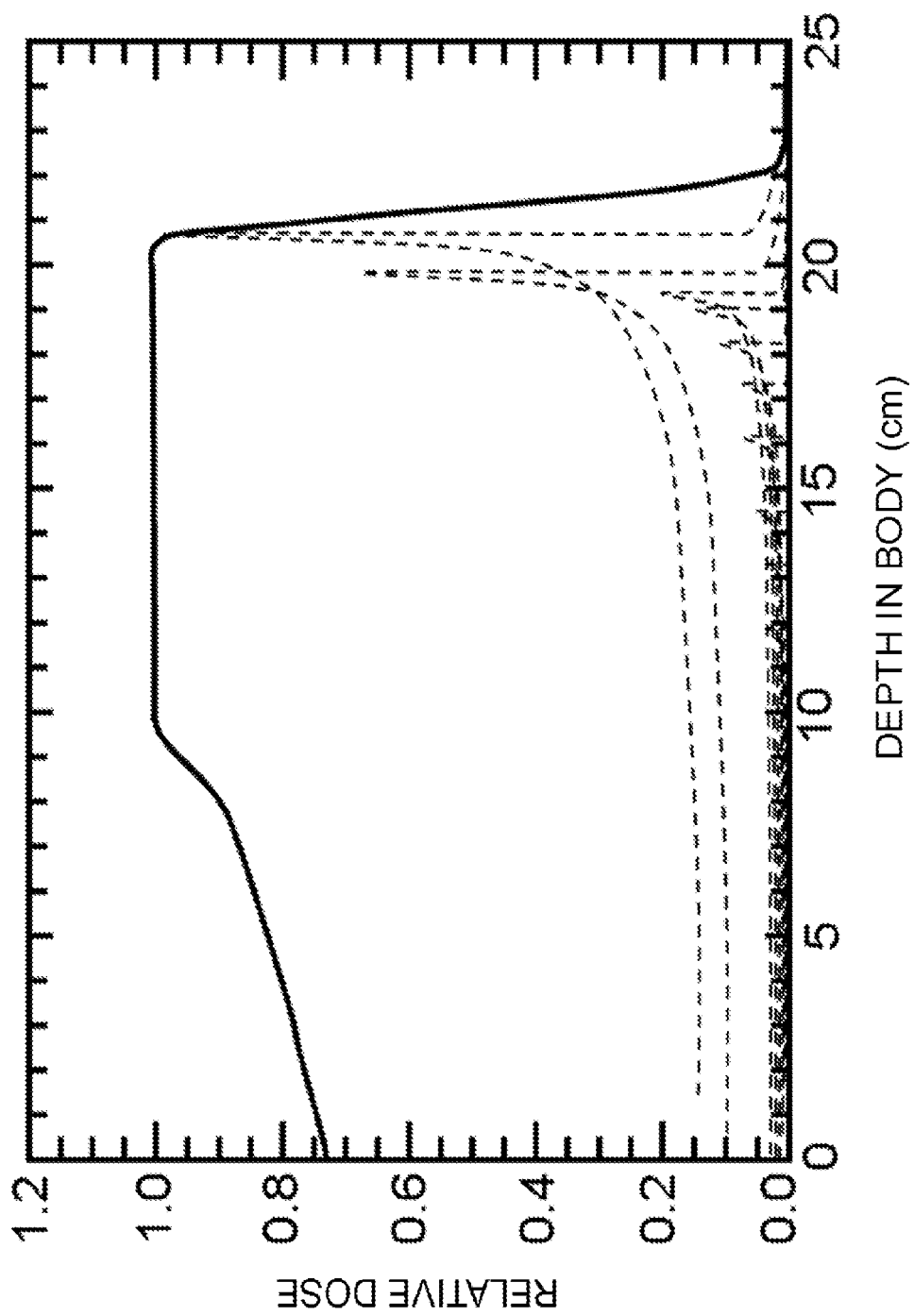
FIG. 15 is a diagram illustrating one example of the dose distribution of each irradiation layer of particle beam and the depth direction dose distribution.
Figure 16:
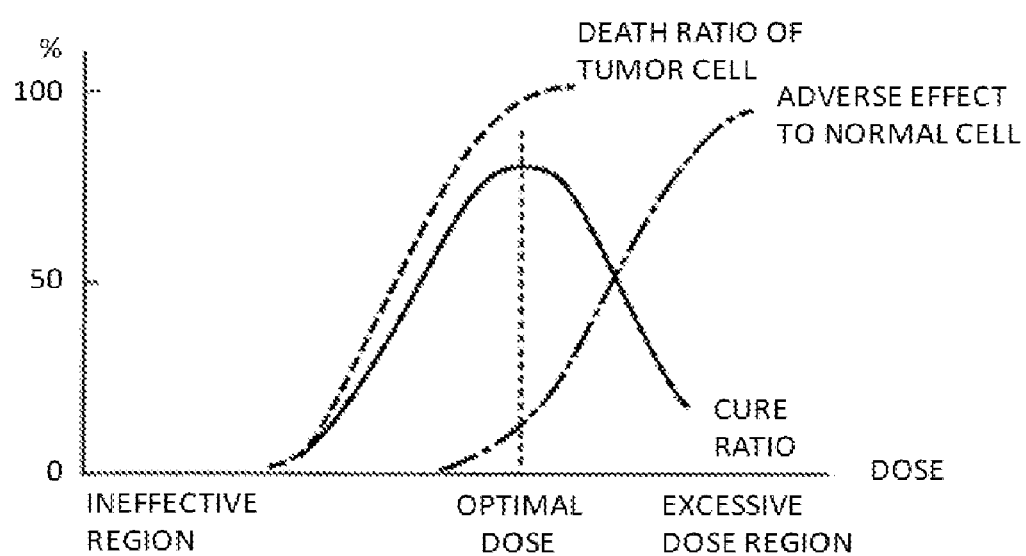
FIG. 16 is a diagram illustrating the death ratio of tumor cell, the ratio of adverse effect of normal cell and the ratio of cure to the irradiation dose of particle beam.

The reason why the irradiation distribution as shown in FIG. 5 is formed is such that in a case where the depth direction irradiation field spread with a spot scanning technique is performed by changing the particle beam energy, it is necessary to perform the irradiation as shown in FIG. 15. That is, in a part which is the deepest layer in an irradiation layer, the dose indicated by a broken line located the rightmost in FIG. 15, that is, the maximum dose is irradiated and in other parts, the depth direction irradiation field spread is performed by irradiating the dose which is one fifth or less of the dose irradiated with the deepest layer. Further, normal cells exist the outside of the deepest layer TVd of irradiation target TV, therefore, it is necessary to suppress the dose given to the part as much as possible. In the peripheral part of the deepest layer TVd, a beam with an irradiation spot having a small diameter that can form a detailed dose distribution is irradiated as shown in FIG. 4C so as to form the dose distribution as shown in FIG. 5. Consequently, the dose distribution at a part immediately outside the deepest layer TVd can be suppressed. By irradiating with an irradiation spot having a small diameter, particularly, even in a case where a border has a complicated shape and even in a case where normal cells which are sensitive to the particle beam exist near the border, a detailed distribution of dose can be formed. Therefore, irradiation can be performed along the outline of the deepest layer TVd more faithfully.

Further, in the present invention, the while region of the Zi layer is irradiated with the irradiation spot S1 having a large beam diameter, and then the peripheral part is irradiated again with the irradiation spot S2 having a small beam diameter. Therefore, unlike the Patent Document 1, a border between an irradiation region irradiated with a particle beam having a large beam diameter and an irradiation region irradiated with a particle beam having a small beam diameter is not generated. According to the irradiation method disclosed by Patent Document 1, it is required to dispose spots to be irradiated with an irradiation spot having a small beam diameter in a region so as to avoid a region which is irradiated with an irradiation spot having a large beam diameter. However, according to the method of the present invention, spots to be irradiated with an irradiation spot having a small beam diameter can be disposed regardless of disposition of spots irradiated with an irradiation spot having a large beam diameter. Consequently, disposition of spots having a small beam diameter becomes simple. Here, since the case of idealized shape, semicircular shape, is examined, a spot corresponding to the deepest layer is generated only outside of the volume, however, in actual, there is a case where a spot corresponding to the deepest layer is also required inside of the irradiation region in a certain cross section. For example, in a case where the lowest part of semicircular shape, that is, the region around "the South Pole" is recessed, the above-mentioned case will be generated. Further, in the above-mentioned case, a beam having a large beam diameter S1 is irradiated first and then a beam having a small diameter S2 is irradiated. However, the order of irradiation may be reverse, that is, a beam having a small beam diameter S2 shown in FIG. 4C may be irradiated first and then a beam having a large beam diameter S1 shown in FIG. 4B may be irradiated. Regardless the order of irradiation, effect is absolutely same.

Embodiment 2

Next, Embodiment 2 of the present invention will be described. In Embodiment 2, respiration measurement of a patient or position detection of an irradiation target is performed, and based on the respiration measurement or the position detection of the irradiation target, a respiration judgment of the patient is performed, and particle beams are irradiated in synchronization with the respiration phase. Since a position of irradiation target is changed by respiration of a patient, an irradiation position of the particle beam is changed. Consequently, the irradiation accuracy is decreased. Particularly, since a part of the deepest layer is a border layer between normal cells and a diseased part, and the dose irradiated with the deepest layer is high, the irradiation dose given to normal cells may increase due to deterioration of the irradiation accuracy. Therefore, particularly, high irradiation accuracy is required in performing irradiation in the deepest layer. Consequently, in the particle beam irradiation system according to Embodiment 2, irradiation with an irradiation spot having a small diameter in Embodiment 1 is performed in synchronization with the respiration phase so as to irradiate at the respiration phase in which change of the position of an irradiation target is small.

Figure 6:
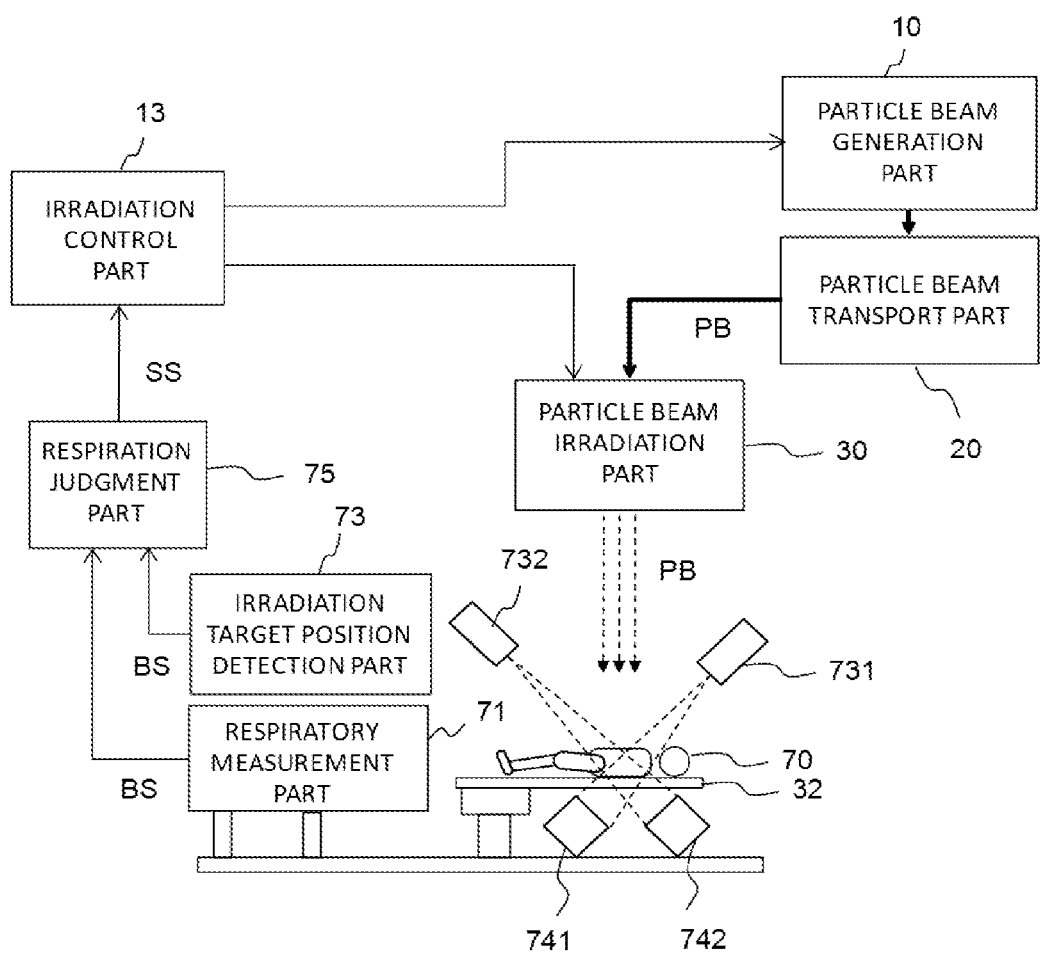
FIG. 6 is a block diagram schematically illustrating the configuration of the particle beam irradiation system according to Embodiment 2 of the present invention.

FIG. 6 is a block diagram schematically illustrating the configuration of the particle beam irradiation system according to Embodiment 2 of the present invention. The particle beam generation part 10 and the particle beam transport part 20 shown in FIG. 6 are same as those shown in FIG. 2. The particle beam irradiation part 30 includes the particle beam irradiation parts 30A and 30B shown in FIG. 2. The particle beam irradiation part 30 has an irradiation nozzle 31, and as the irradiation nozzle 31, the irradiation nozzle 31 used in Embodiment 1 shown in FIG. 1 is used.

A respiratory measurement part 71 measures the breath of the patient 70 and outputs a respiratory signal BS, and what is used in conventional particle beam irradiation system or an X-ray CT can be used. As the respiratory measurement part 71, it is possible to use a method in which a light-emitting diode (LED) is attached to the abdominal region or the chest region of the patient 70 and the breath is measured by the displacement of the light emitting position of the light emitting diode, a method in which a reflecting device is used and the displacement of the body is measured by a laser beam, a method in which an extensible resistor is attached to the abdominal region of the patient and a change of the electric characteristics is measured, a method in which the breath of the patient 70 is directly measured, or the like.

An irradiation target position detection part 73 detects the position of the irradiation target TV in the patient 70 and outputs a respiratory signal BS. As the irradiation target position detection part 73, X-ray sources 731 and 732, and X-ray image acquisition devices 741 and 742 corresponding to these are used. The X-ray sources 731 and 732 irradiate X-rays to the irradiation target TV in the patient 70, and the X-ray image acquisition devices 741 and 742 acquire images of X-rays from the X-ray sources 731 and 732, and detect the position of the irradiation target TV. As the X-ray image acquisition devices 741 and 742, for example, an X-ray television apparatus using an image intensifier, means for measuring a scintillator plate by a CCD camera, or the like is used. With respect to the irradiation target TV, there is a method of burying a small piece of metal, such as gold, as a marker, and it becomes easy to specify the position of the irradiation target TV by using this marker.

Both the respiration measurement part 71 and the irradiation target position detection device 73 detect the displacement of the irradiation target TV due to the breath, and generate the respiratory signals BS. Both the respiratory signals BS are inputted to a respiration judgment part 75 (may be called as a displacement detector). The respiration judgment part 75 judges, based on the correlation of exhalation/inspiration stored in its memory, the displacement of respiration in real time from the inputted respiratory signals BS, and outputs a status signal SS to the irradiation control part 13.

Figure 7:
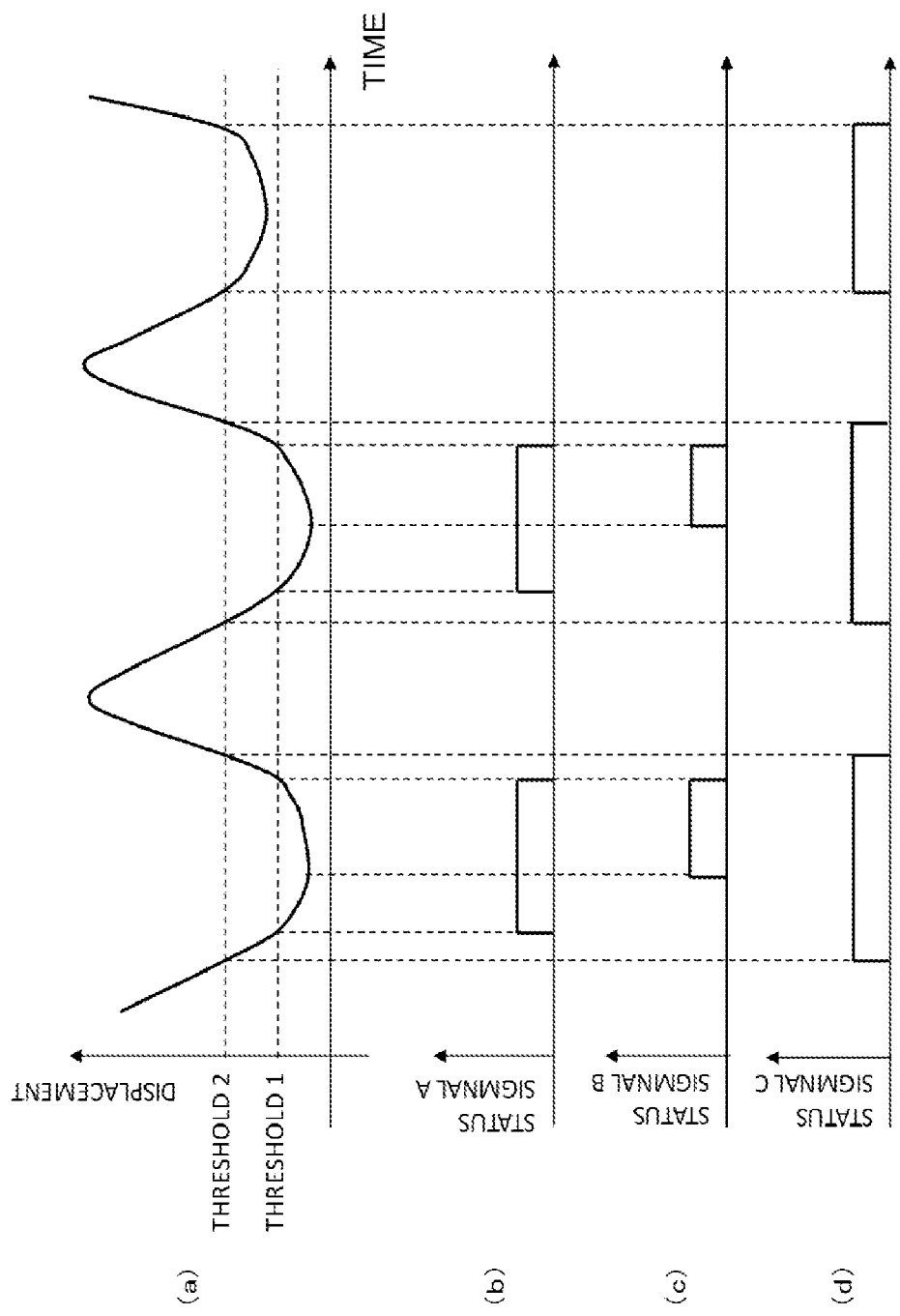
FIG. 7 is a diagrammatic view illustrating the operation of particle beam irradiation system according to Embodiment 2 of the present invention.

The above-mentioned operation will be shown in FIG. 7 as a line diagram. In FIG. 7, a line diagram (a) shows the respiration displacement of an irradiation target, for example, line diagrams (b), (c), and (d) show a status signal that is obtained by judging based on the respiration displacement. In FIG. 7 (a), two horizontal broken lines indicate two predetermined threshold values. In a case where the displacement is less than the predetermined threshold value, the respiration judgment part 75 outputs the status signal indicated by a line diagram shown in FIGS. 7 (b), (c) and (d), that is, the signal indicating such that a state where a particle beam can irradiate.

The irradiation control part 13 performs the spot irradiation with the irradiation spot S2 having a small beam diameter and with the irradiation spot S1 having a large beam diameter based on the status signal, as described Embodiment 1. When the status signal A in FIG. 7(b), that is, the status signal in a case where the displacement is less than a threshold indicated by threshold 1 in FIG. 7(a) is outputted, the irradiation performed with the irradiation spot S2 having a small beam diameter is performed. And when the displacement is more than the threshold 1, the irradiation performed with the irradiation spot S2 having a small beam diameter is not performed. Further, in some diseased parts, irradiation may be performed only when the differential value of the displacement is positive. This is because the displacement is measured on a surface of body, and in some cases, the measured displacement may not correspond to the movement of patient accurately. The status signal of the above-mentioned case is indicated by status signal B in FIG. 7(c).

On the other hand, the irradiation with the irradiation spot S1 having a large beam diameter may be performed regardless of the respiration displacement. Regarding the irradiation with the irradiation spot S1, the dose of the irradiation is small even at the deepest layer. Therefore, even if the irradiation is performed in a case where the irradiation accuracy is low due to large displacement and irradiation is performed on normal cells, the dose of irradiation given to the normal cells is small. Further, in irradiating the irradiation target TV other than the deepest layer, the irradiation accuracy is not required so much. On the other hand, the irradiation with the irradiation spot S2 having a small beam diameter is performed at the deepest layer and the dose of the irradiation per unit volume is large. Therefore, when the irradiation with the irradiation spot S2 is performed in a case where the displacement is large, there is a possibility such that the dose of irradiation given to normal cells is large. Consequently, as above-mentioned, the dose of irradiation given to normal cells can be suppressed by performing the irradiation with the irradiation spot S2 only when the respiration displacement is less than a predetermined threshold value. In addition to that, the irradiation with the irradiation spot S1 may be performed regardless of the respiration displacement. Therefore, the increase of the irradiation time for whole of the irradiation target can be suppressed.

When the irradiation with the irradiation spot S1 is performed corresponding to the respiration displacement, the irradiation time as a whole increases. However, it is needless to say that the irradiation having higher accuracy can be performed. In this case, in comparison with the irradiation using the irradiation spot S2, the irradiation with the irradiation spot S1 can set a threshold of the respiration displacement that allows the irradiation to be mild. A status signal is created by a threshold that is milder than the threshold 1, for example, the threshold 2 shown in FIG. 7(a), and the irradiation with the irradiation spot S1 is performed corresponding to the status signal C shown in FIG. 7(b). With respect to the irradiation spot S2, the irradiation having good accuracy is performed by setting a threshold to be the threshold 1 that is stricter than the threshold 2, or by limiting to the case in which the time-differential of the displacement is positive, that is, the displacement curve line is right-upward. As above-mentioned, it is preferable that the conditions that allow the irradiation with the irradiation spot S1 having a large beam diameter and the irradiation with the irradiation spot S2 having a small beam diameter are set as appropriate. Accordingly, the irradiation time can be shortened in comparison with the case in which all dose of the irradiation is performed with the irradiation spot S2. Consequently, irradiation in which a high dose region is matched well with TVd can be realized.

Embodiment 3

Figure 8:
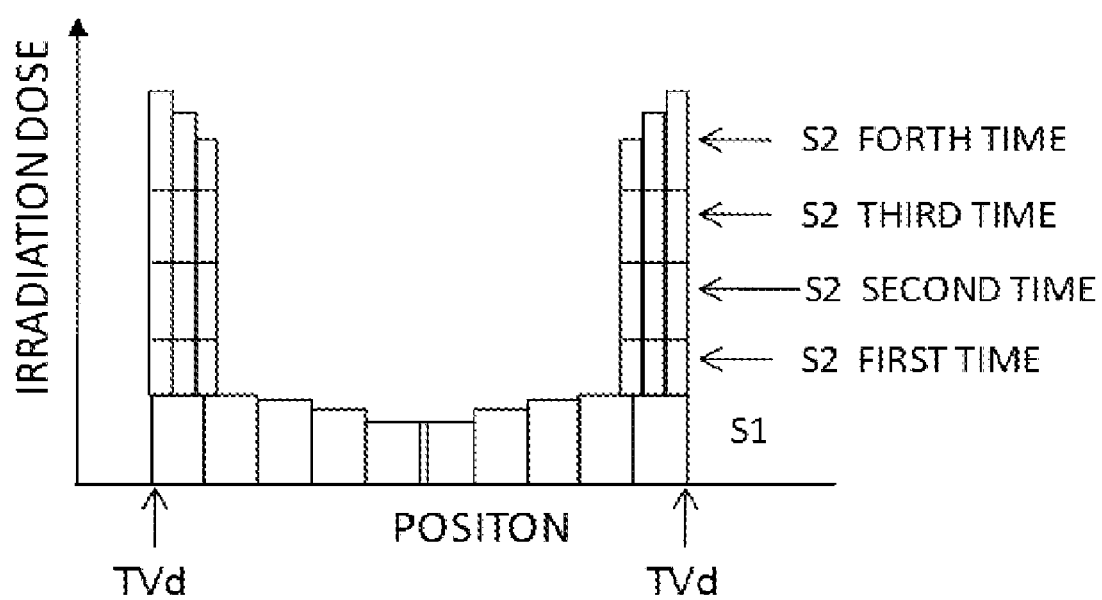
FIG. 8 is a diagram for explaining the irradiation dose irradiated by the control method of particle beam irradiation system according to Embodiment 3 of the present invention.

FIG. 8 shows a method of controlling the particle beam irradiation system according to Embodiment 3. In Embodiment 1, the irradiation with the irradiation spot S2 having a small beam diameter is performed once at each position in the deepest layer. However, in Embodiment 3, the irradiation with the irradiation spot S2 is performed at each spot position in the deepest layer plural times.

In the same way as that of FIG. 5, FIG. 8 shows the dose distribution in the Zi layer on a line A-A shown in FIGS. 4B and 4C in Embodiment 3. In FIG. 7, the horizontal axis indicates a position in a line A-A shown in FIGS. 4B and 4C, and the vertical axis indicates the irradiation dose at the position. In Embodiment 3, in the same way as that of Embodiment 1 shown in FIG. 5, a degree of a required amount of dose for a part of the Zi layer other than the deepest layer is irradiated including the peripheral part of the deepest layer without significantly changing the irradiation dose (per unit area) irradiated with the irradiation spot S1. The irradiation with the irradiation spot S2 is only performed in the deepest layer part of the Zi layer, and the total dose in which the dose applied by the irradiation spot S2 and that applied by the irradiation spot S1 is combined is made to be the required amount of dose to be applied to the part. In Embodiment 3, the irradiation dose applied by the irradiation spot S2 having a small beam diameter is divided into four-times. Therefore, the dose applied by the irradiation spot S2 per one irradiation is small.

Figure 9A:
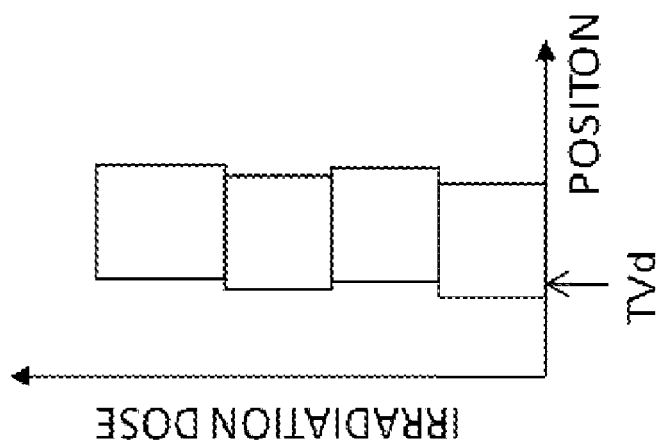
FIG. 9 is a diagram for explaining the effect of irradiation applied by the control method of particle beam irradiation system according to Embodiment 3 of the present invention.
Figure 9B:
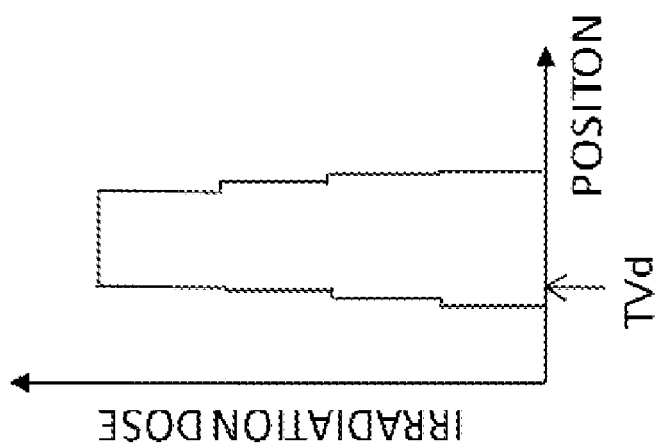
Figure 9C:
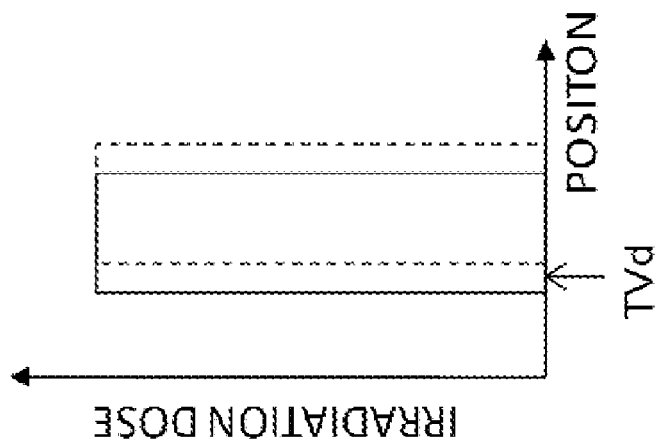

FIG. 9 shows the effect obtained by the irradiation method in Embodiment 3. FIG. 9A and FIG. 9B show the dose distribution applied by the irradiation spot S2 according to the irradiation method in Embodiment 3 and FIG. 9C shows the dose distribution in a case where the target dose is reached by one-irradiation in the same way as that of Embodiment 1. The horizontal axis indicates the lateral direction of the irradiation target TV, for example, a position in an X-axis direction and the vertical axis indicates the irradiation dose. FIG. 9A and FIG. 9B show the irradiation dose applied by the irradiation according to Embodiment 3 by different ways of displaying. The irradiation dose is divided to apply in four times and in FIG. 9A, the divided irradiation dose is shown intelligibly by displaying four squares that are stacked up. In FIG. 9A, from the bottom, the irradiation dose of the first irradiation, that of the second irradiation, that of the third irradiation and that of the fourth irradiation are shown, and FIG. 9A shows that irradiation position at each time is deviated slightly. Since a patient moves in breathing, etc., the irradiation position deviates slightly at each time of irradiation as shown in FIG. 9A. When the irradiation dose for four times is accumulated at each position, the dose distribution as shown in FIG. 9B is obtained. The dose shows the distribution in which the dose decreases from the center to the peripheral part. In FIG. 9C, a solid line indicates the dose distribution in which one irradiation is performed in certain time, and a broken line indicates the dose distribution in which one irradiation is performed in another time. As shown in FIG., the position deviation directly affects the dose distribution. For example, as indicated by a solid line shown in FIG. 9C, when the irradiation position deviates to the side of normal cells which exist directly outside the deepest part TVd and the irradiation is performed, the irradiation dose applied to the normal cells becomes large. On the other hand, according to the dose distribution performed by the irradiation method in Embodiment 3, that is, FIG. 9A and FIG. 9B, when a border position TVd of the deepest part is a position indicated by TVd, the dose applied to normal cells which exist directly outside the position is less than the dose indicated by a solid line in FIG. 9C. Consequently, the effect to the normal cells is small.

Embodiment 4

Figures 10A, 10B:
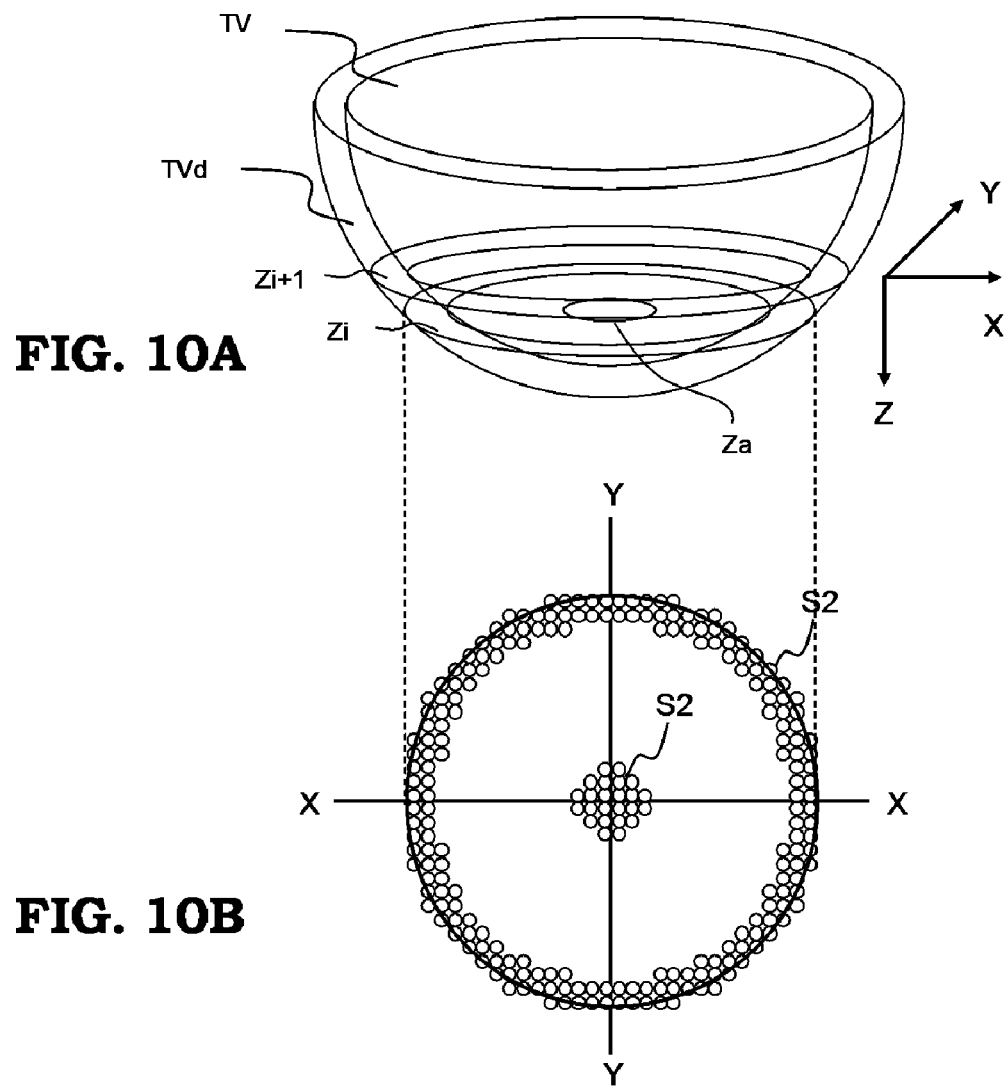
FIG. 10 is schematic diagram for explaining the control method of particle beam irradiation system according to Embodiment 4 of the present invention.

Since in Embodiments 1 to 3, large dose distribution is applied to the deepest part, large dose is applied precisely to the deepest part by a beam with the irradiation spot S2 having a small beam diameter. However, in some cases of diseased part, large dose distribution is required to apply to a part other than the deepest part. For example, cancer has a region in which a cell having high radiation resistance exists at a center of tumor of Za in the Zi layer as shown in FIG. 10A. FIG. 10B is a diagram showing the irradiation with the irradiation spot S2 having a small spot diameter that is applied to a layer indicated by Zi layer in FIG. 10A. As shown in FIG. 10B, not only the peripheral part that is the deepest part, but also the region of Za, irradiation with the irradiation spot S2 having a small spot diameter is applied so as to form the irradiation dose distribution with large dose in the region of Za.

Embodiment 5

Figure 11A:
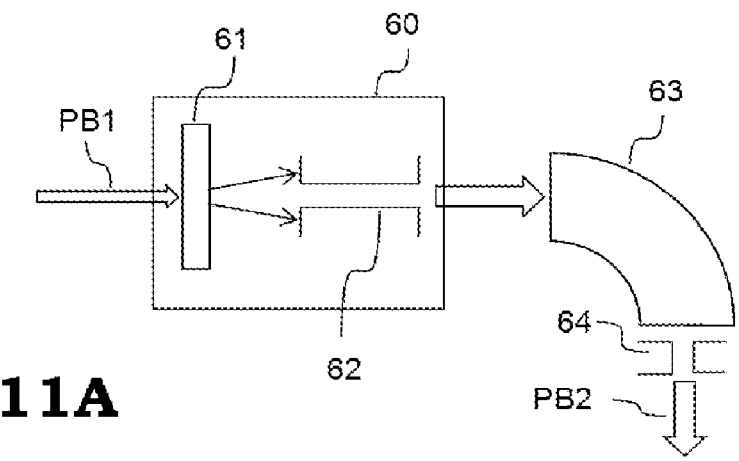
FIG. 11 is a diagram schematically illustrating one example of beam diameter changer of particle beam irradiation system according to Embodiment 5 of the present invention.
Figure 11B:
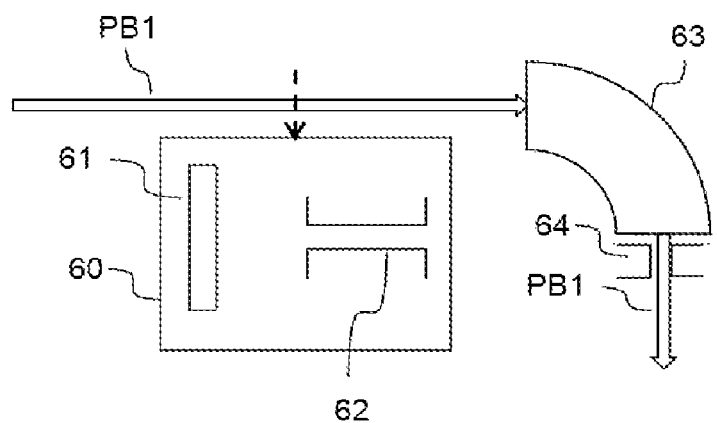

In Embodiment 1, the beam diameter is changed by four-pole magnet; however, the beam diameter may be changed by other means. FIG. 11A shows another example of beam diameter changer that changes the beam diameter. Numeral 60 indicates a beam diameter changer comprising a scatter 61 and a collimator 62. When a beam having a small diameter PB1 is incident on the scatter 61, the beam is scattered forward to be a diverging beam. When the diverging beam is passed through the collimator 62, the beam diameter of the beam PB1 is changed to the beam diameter of the beam PB2, which is larger than PB1. The parameter of the scatter 61 and the collimator 62 are set for the beam diameter of the beam PB1 in a state where the beam is not passed through the beam diameter changer 60 to be the small diameter S2 in Embodiments 1 to 3; and the parameter of the scatter 61 and the collimator 62 those are set for the beam diameter which is passed through the beam diameter changer 60 to be S1. The beam diameter changer 60 may provide on the irradiation nozzle 31 or on the particle beam transport part 20, and the beam diameter changer 60 is provided movably on the passage of beam. By moving the beam diameter changer 60, the beam is controlled to pass through the beam diameter changer 60 so as to be the beam diameter S1, and the beam is controlled not to pass through the beam diameter changer 60 so as to be the beam diameter S2. When a beam having a large beam diameter in Embodiments 1 to 3 is irradiated, as shown in FIG. 11A, a beam that is passed through the beam diameter changer 60 is irradiated. When a beam having a small beam diameter is irradiated, as shown in FIG. 11B, the beam diameter changer 60 is moved as shown by the arrow, and a beam having the state of PB1 is irradiated. The movement of the beam diameter changer 60 is controlled by the signal that is transmitted from the beam diameter controller 15 of the irradiation control part 13.

Further, a deflection electromagnet 63 is provided in the downstream of the beam diameter changer 60 so as to deflect the beam. When a beam passes through the scatter 61, the energy width is spread. The deflection electromagnet 63 and the collimator 64 are provided to form an energy analysis part. The beam is deflected by the deflection electromagnet 63 and uneven beam energy is trimmed by the collimator 64 so as to be the beam having an even energy. Consequently, the beam that is appropriate for using the particle beam therapy can be obtained. When the decrease of the beam energy caused by passing the beam through the scatter 61 becomes a problem, the amount of beam energy that is decreased by the scatter 61 of the beam diameter changer 60 may be complemented, for example, by increasing the amount of beam energy that is generated in the particle beam generation part 10.

Embodiment 6

Figure 12:
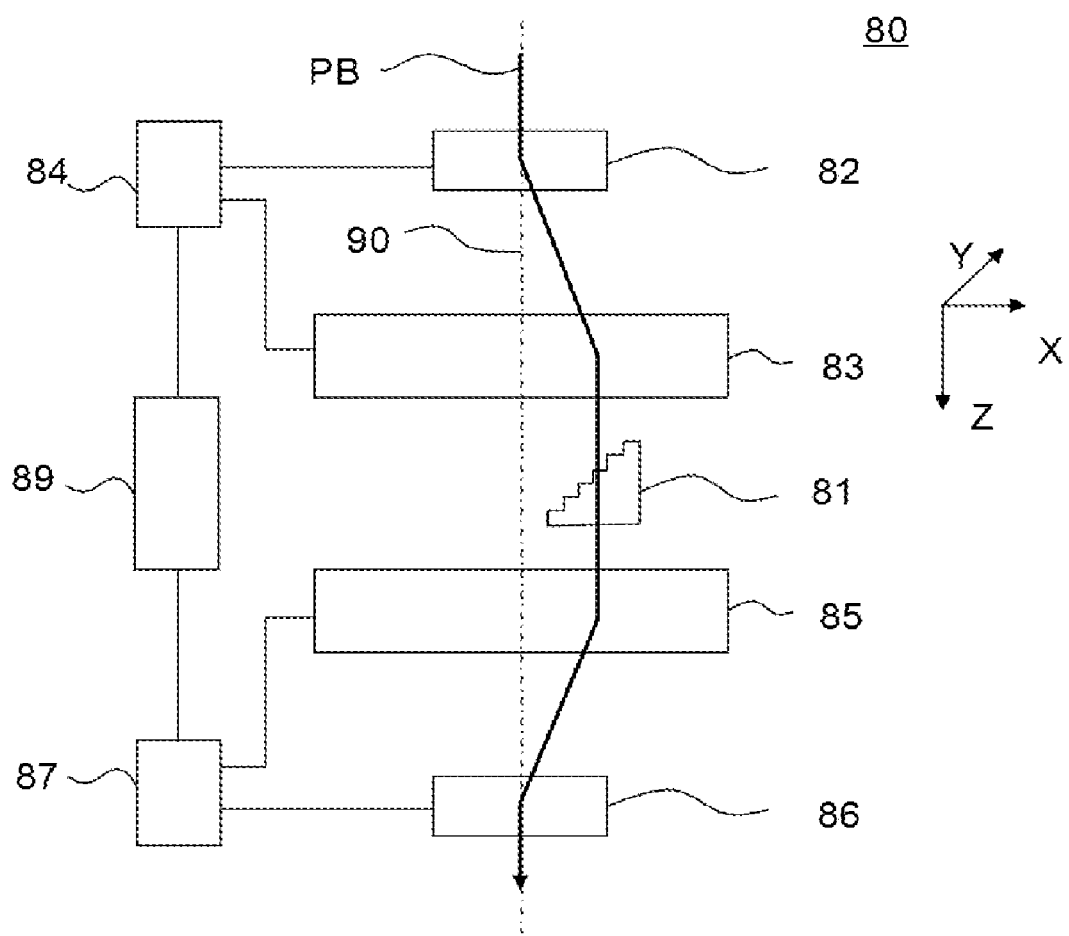
FIG. 12 is a block diagram illustrating the configuration of the irradiation nozzle in which an energy changing device of particle beam irradiation system according to Embodiment 6 of the present invention is used.

In Embodiment 1, the particle beam energy is changed in a particle beam generation part, however, an energy changer may be provided in the middle of the passage of beam so as to change the energy. FIG. 12 shows the configuration of one example of an energy changer. The energy changer 80 comprises a range shifter 81 having the thickness that changes in stepwise to the width direction (X direction); deflection electromagnets 82 and 83 that constitute a pair of deflection electromagnets that are provided at the upstream for changing the position of the charged particle beam PB that passes through the range shifter 81; a first deflection electromagnet power source 84 that excites the pair of deflection electromagnets that are provided at the upstream; a deflection electromagnet 85 and 86 that constitute a pair of deflection electromagnets that are provided at the downstream for returning the charged particle beam PB that passed through the range shifter 81 to the original trajectory; a second deflection electromagnet power source 87 that excites the pair of deflection electromagnets that are provided at the downstream; and a deflection control part 89 that calculates the moving amount of the charged particle beam in the trajectory caused by the pair of deflection electromagnets that are provided at the upstream, based on the energy command value that is input from the energy setting controller 14 of the irradiation control part 13, to transmit the exciting current value to the first deflection electromagnet power source 83. The deflecting control part 89 also controls the second deflection electromagnet power source 87.

The charged particle beam PB is incident on the pair of deflection electromagnets that are provided on the upstream on the beam axis 90 (Z axis). The trajectory of the charged particle beam PB is moved to the horizontal direction (X direction) on the plane of paper of FIG. 12. The deflection electromagnet 82 is a deflection electromagnet for changing the trajectory and the deflection electromagnet 83 is a deflection electromagnet for parallelizing the trajectory. The deflection electromagnet 82 for changing the trajectory deflects the trajectory of incident charged particle beam PB to be inclined at a predetermined angle θ to the Z axis. The deflection electromagnet for parallelizing the trajectory 83 deflects the charged particle beam PB that is inclined at a predetermined angle to the Z axis by the deflection electromagnet for changing the trajectory 82 to be parallel to the Z axis. On the downstream of the range shifter 81, the charged particle beam PB is returned to the beam axis 90 (Z axis) by the deflection electromagnet for changing the trajectory 85 and a deflection electromagnet for parallelizing the trajectory 86. The deflection electromagnet for changing the trajectory 85 deflects the charged particle beam PB to be inclined at a predetermined angle to the Z axis. The deflection electromagnet for parallelizing the trajectory 86 deflects the trajectory that is inclined to the Z axis by the deflection electromagnet for deflecting the trajectory 85 to the trajectory on the Z axis.

The operation of the energy changer 80 will be described. The charged particle beam PB that is guided to the energy changer 80 is deflected by the pair of deflection electromagnets 82 and 83 that are provided on the upstream and moves on the trajectory that is parallel to the Z axis and being apart from the Z axis by a predetermined distance to the X direction. Then, when the charged particle beam PB passes through a part of the range shifter 81 having a predetermined thickness, the energy of the charged particle beam PB is reduced in proportion to the thickness. As a result, the energy of the charged particle beam becomes desired. The charged particle beam PB whose energy is changed to the desired amount by the above-mentioned procedure is returned by the pair of the deflection electromagnets 85 and 86 that are provided on the downstream to the extension of the original trajectory of the charged particle beam PB which is incident on the energy changer 80. The energy changer 80 has the merits such that the driving sound is not generated for driving the range shifter in changing the energy of the particle beam and changing the range of the particle beam.

Figure 13:
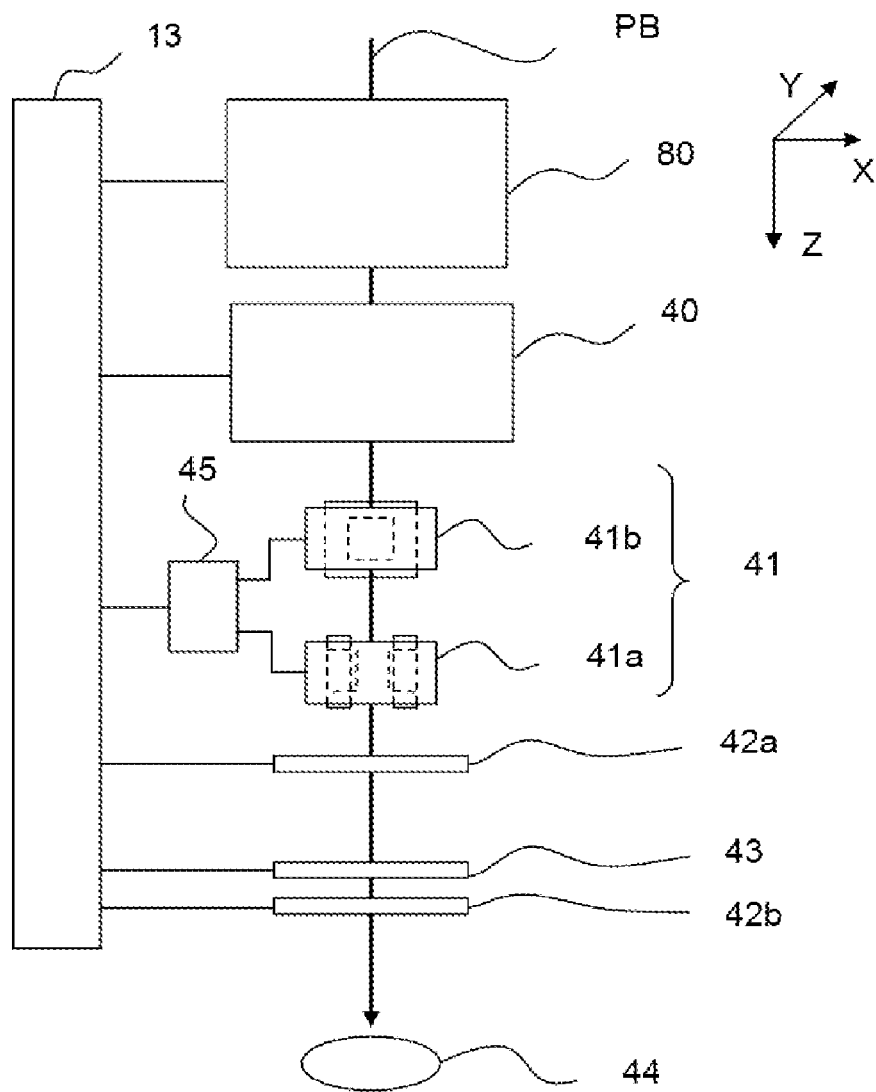
FIG. 13 is a block diagram illustrating the configuration of the irradiation nozzle of particle beam irradiation system according to Embodiment 6 of the present invention in which an energy changing device shown in FIG. 12 is used.
Figure 14:
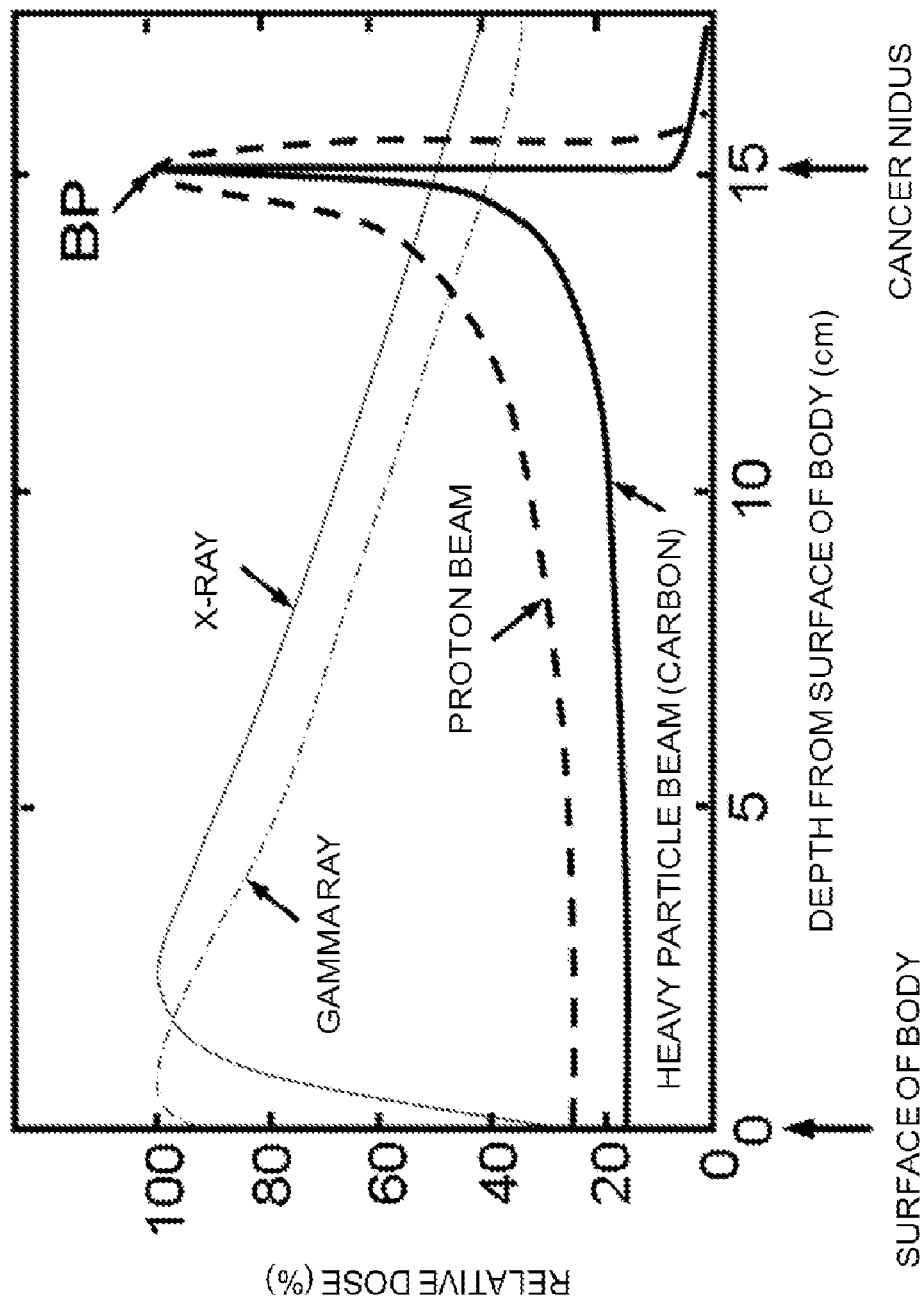
FIG. 14 is a diagram illustrating the dose distribution of radiation beams in the human body in a case where various kinds of radiation beams are irradiated on to the human body.

FIG. 13 is a block diagram showing the configuration of the irradiation nozzle 31 in which the energy changer 80 according to the particle beam irradiation system in Embodiment 6, and same symbol as that of FIG. 3 indicates the same part or the corresponding part. The energy changer 80 is provided, for example, on the upstream of the beam diameter changer 40. The energy changer 80 is controlled by the signal that is transmitted from the energy setting controller 14, the energy of the particle beam to be irradiated on the irradiation target is set to a predetermined amount of energy so as to irradiate on the irradiation target. That is, irradiation is performed at each irradiation layer at every changing the energy.

When the spread energy of the beam after the beam is passed through the energy changer 80 becomes a problem, it is preferable such that a deflection electromagnet and a collimator are provided downstream of the energy changer 80 to form an energy analysis part in the same way as that of Embodiment 5 so as to obtain the beam having uniform energy. Further, energy may be set by both an accelerator and an energy changer. In a case where the energy is set by using both of an accelerator and an energy changer, more detail setting of energy can be performed.

DESCRIPTION OF REFERENCE NUMERALS AND SIGNS 1, 2: treatment room
10: particle beam generation part
11: ion source
12: accelerator
13: irradiation control part 14: energy setting controller
15: beam diameter controller
16: beam scanning controller
20: particle beam transport part
30A, 30B: particle beam irradiation part
31: irradiation nozzle
32: treatment table
32: positioning device
40, 60: beam diameter changer
41: lateral direction irradiation field spread part (beam scanner)
41A, 41B: deflection electromagnet for scanning
42A, 42B: beam position monitor
43: dose monitor
44: irradiation target
50: deflection electromagnet
80: energy changer
75: respiration judgment part (displacement detector)
PB: particle beam

The invention claimed is:

1. A particle beam irradiation system comprising:
a particle beam generation part;
a particle beam irradiation part where a charged particle beam that is generated in the particle beam generation part is irradiated on an irradiation target and;
an irradiation control part that controls the charged particle beam to be irradiated;
wherein the particle beam irradiation part comprises:
a beam scanner that scans the charged particle beam laterally in two dimensions that is perpendicular to the irradiation direction of the charged particle beam; and a beam diameter changer that changes the beam diameter of the charged particle beam;
wherein the irradiation control part comprises: an energy setting controller that sets the energy of the charged particle beam;
a beam scanning controller that controls the beam scanner; and
a beam diameter controller that controls the beam diameter changer;
wherein the irradiation control part sets the beam diameter of the charged particle beam by the beam diameter controller to be a first beam diameter, the charged particle beam is scanned step-wise by the beam scanning controller so as to irradiate the charged particle beam on a predetermined region of the irradiation target, after that, the beam diameter of the charged particle beam is set by the beam diameter controller to be a second diameter that is different from the first beam diameter, and the charged particle beam is scanned step-wise by the beam scan controller so as to control the charged particle beam to irradiate on a region that is overlapped with at least a part of the predetermined part of the irradiation target.

2. The particle beam irradiation system according to claim 1, wherein the region irradiated by the beam having the smaller diameter between the first beam and the second beam is narrower than the region irradiated with the beam having the larger diameter between the first beam and the second beam.

3. The particle beam irradiation system according to claim 2, further comprising a displacement detector to detect a displacement of the irradiation target,
wherein the irradiation control part controls the irradiation with the small beam diameter corresponding to the output signal transmitted from the displacement detector.

4. The particle beam irradiation system according to claim 3,
wherein the irradiation control part controls the irradiation in which the beam having the larger beam diameter is irradiated under the condition that irradiation permission condition for irradiation with the beam having the larger beam diameter is less strict compared to the irradiation permission condition for irradiation with the beam having the smaller diameter corresponding to the output signal transmitted from the displacement detector.

5. The particle beam irradiation system according to claim 2, wherein the irradiation control part controls to irradiate with a beam having small beam diameter plural times at the same irradiation region.

6. A method for controlling a particle beam irradiation system in which a charged particle beam that is generated in a particle generation part is irradiated on an irradiation target,
wherein a beam diameter of the charged particle beam is set to be a first beam diameter,
the charged particle beam is scanned step-wise so as to irradiate the charged particle beam on a predetermined region of the irradiation target, after that, the beam diameter of the charged particle beam is set to be a second diameter that is different from the first diameter, and the charged particle beam is scanned step-wise so as to control the charged particle beam to irradiate on a region that is overlapped with at least a part of the predetermined part of the irradiation target.

7. The method for controlling the particle beam irradiation system according to claim 6, wherein the region irradiated by the beam having the smaller diameter between the first beam and the second beam is narrower than the region irradiated with the beam having the larger diameter between the first beam and the second beam.

8. The method for controlling the particle beam irradiation system according to claim 7, wherein the irradiation with the small beam diameter is controlled to perform corresponding to the displacement of the irradiation target.

9. A method for controlling the particle beam irradiation system according to claim 7, wherein the irradiation with the small beam diameter is controlled to perform plural times at the same irradiation region.

* * * * *